United States Patent [19]
Baker

[11] Patent Number: 6,088,837
[45] Date of Patent: Jul. 18, 2000

[54] HEADGEAR WITH PIVOTABLE VISOR

[75] Inventor: Melvin L. Baker, Dublin, Tex.

[73] Assignee: Melrose Corporation, Dublin, Tex.

[21] Appl. No.: 09/157,805

[22] Filed: Sep. 21, 1998

[51] Int. Cl.[7] ...................................................... A42B 1/06
[52] U.S. Cl. ........................................ 2/195.1; 2/10; 2/12
[58] Field of Search ................................ 2/10, 195.1, 12, 2/15

[56] References Cited

U.S. PATENT DOCUMENTS

| 2,342,377 | 2/1944 | Small | 2/12 |
| 5,343,568 | 9/1994 | May | 2/195.1 |
| 5,715,030 | 2/1998 | Quaresima | 2/12 |

Primary Examiner—Diana Oleksa
Attorney, Agent, or Firm—Jeffrey T. Hubbard; H. Denise Kelly; Timmons & Kelly

[57] ABSTRACT

A cap includes a visor having a fixed rear section attached to the crown and a fore section pivotally attached to the rear section. Functionally identical latches, made up of pairs of fingers and mating catches with prongs that engage the finger in a ratchet-and-pawl action, act to engage the pivotable section and hold it vertically up or down, depending on which prongs engage the fingers. An alternative embodiment employs an adjustable headband rather than a cap and crown.

19 Claims, 3 Drawing Sheets

Fig.8

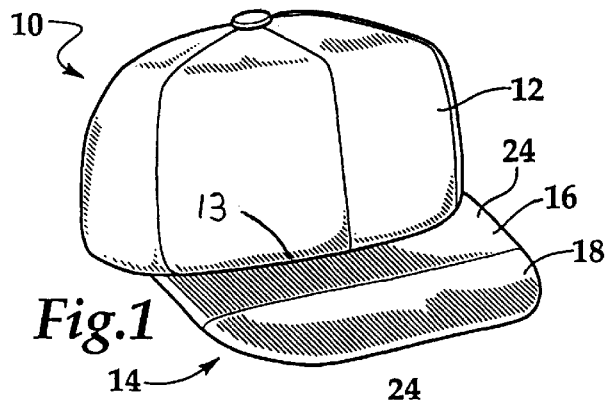
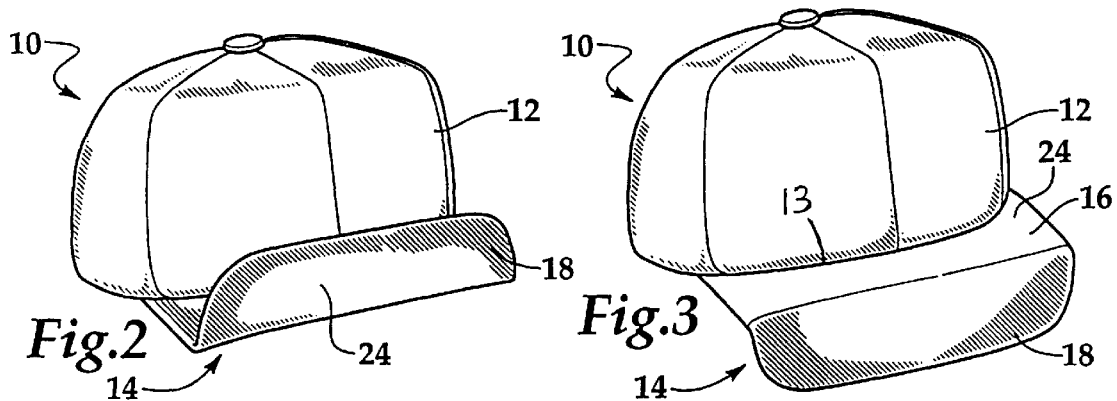
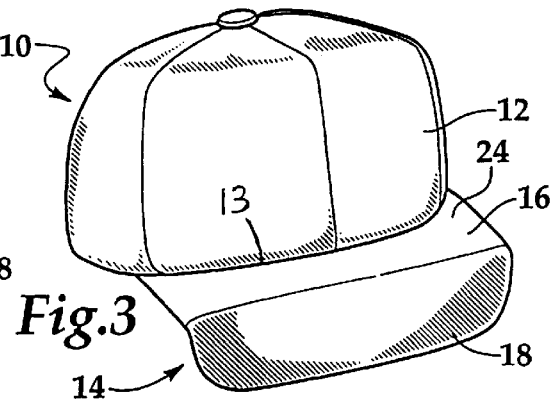
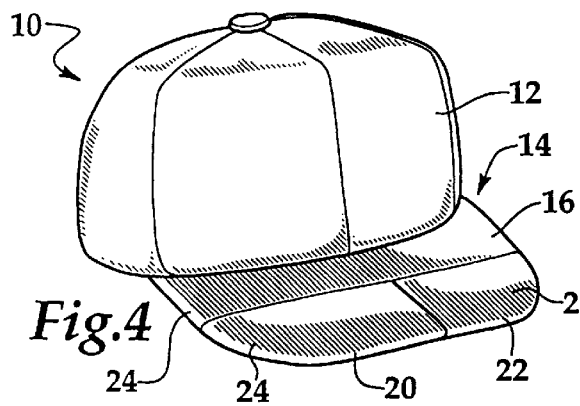
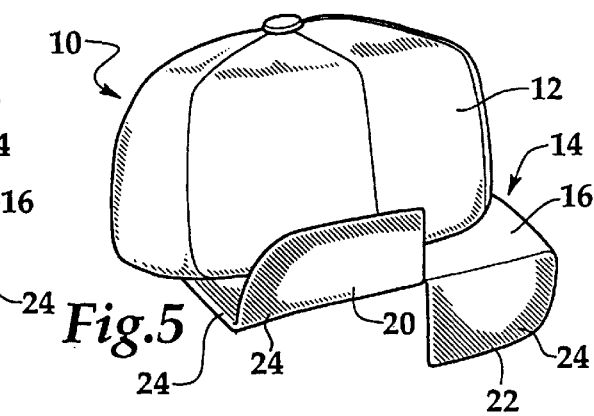
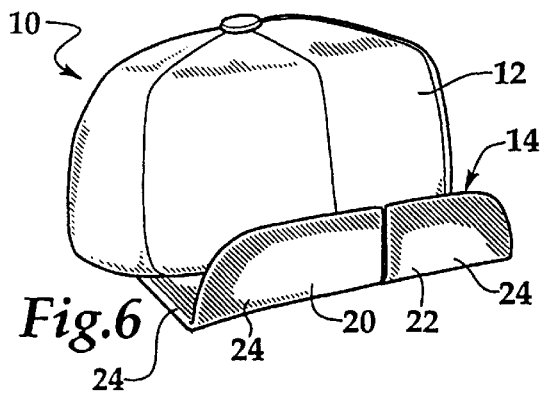
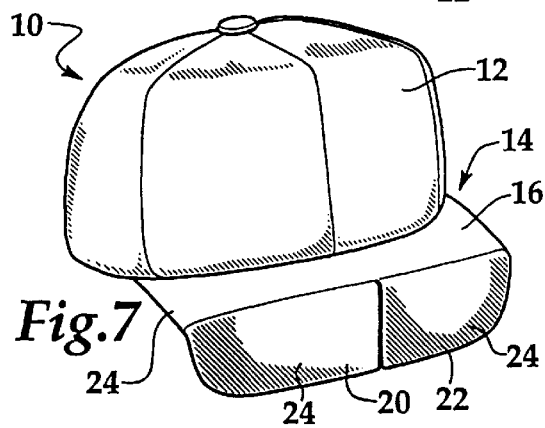

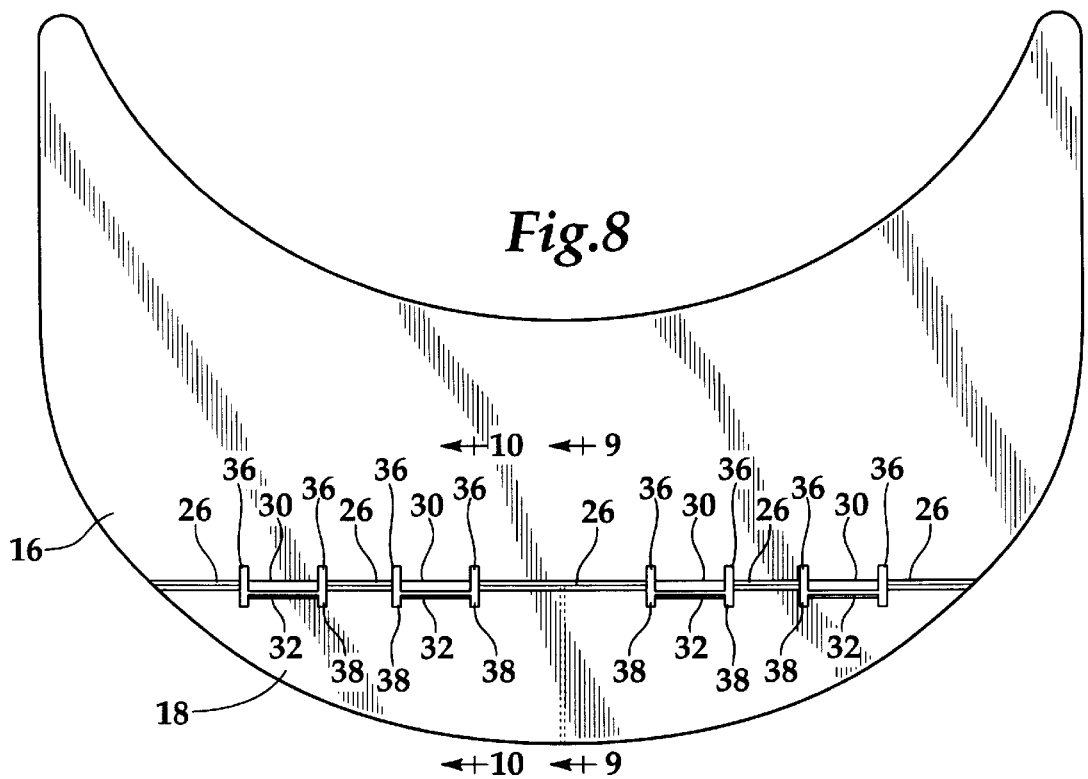
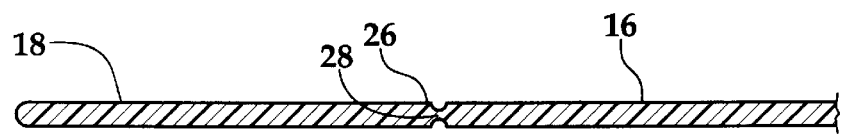
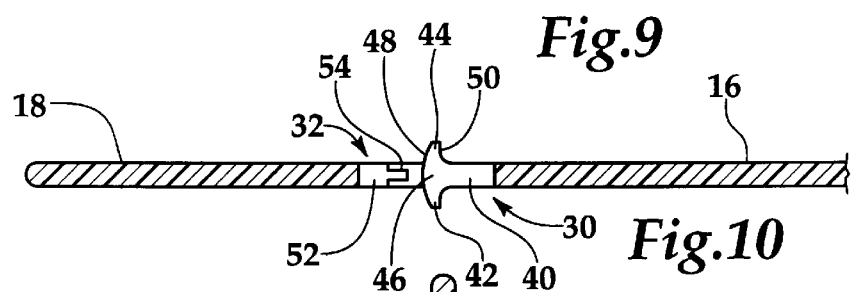
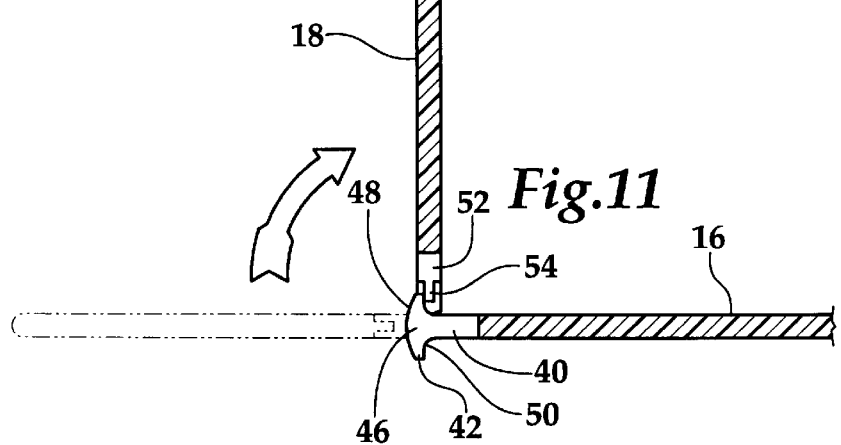

HEADGEAR WITH PIVOTABLE VISOR

BACKGROUND OF THE INVENTION

1. Field of the Invention

This invention relates in general to headgear. In particular, the invention relates to an improved visor, or cap and visor, where the visor has a portion that can be pivoted and set in one of several fixed positions.

2. Description of the Related Art

Visored caps have long been used to keep the sun out of the wearer's eyes for outdoor sports, and have become a fashion accessory in their own right. The advantages of using the crown of a cap to display logos, messages, and even advertising are widely recognized. Placing such messages on the visor has little effectiveness however, because the visor is substantially horizontal, and therefore not favorably inclined for viewing under normal conditions. The traditional horizontal bill that forms the visor for a conventional cap can also fail to provide adequate protection from glare and sun in some cases, such as late afternoon outdoor viewing.

A number of devices have been created to address the need for added protection from glare and direct sunlight. These devices are mostly in the nature of add-on devices that clip, screw, or otherwise attach to the bill/brim of a cap or hat. Since they were not designed to be part of the headgear from the beginning, the resulting combination is often unattractive, even tacky in appearance. Also, many of the add-on devices by their nature can be easily knocked off the headgear, so that the user finds it necessary to remove and store the device when putting the headgear away, which becomes tedious over time. Examples of devices with these disadvantages are disclosed in U.S. Pat. No. 1,665,513, issued to Thomas on Apr. 10, 1928, U.S. Pat. No. 2,654,089, issued to Tannenbaum on Oct. 6, 1953, and U.S. Pat. No. 5,491,841, issued to Valletta on Feb. 20, 1996.

Thus, a need remains for headgear having a visor that can be adjusted for improved protection from glare and sun, and for favorably displaying pictures and text. Such a piece of headgear should have an integral construction, both for providing pleasing aesthetics and to prevent the possibility of losing removable attachments. As always, a device that is simple in structure and inexpensive to manufacture is also desired.

SUMMARY OF THE INVENTION

The general object of the invention is to shade the user's eyes from glare and bright light. Another object is to display pictures and text on a visor that are more easily viewed than on a conventional visor.

In general, these objects are achieved by headgear having a visor with at least one pivotable section. In the preferred embodiment, the front section of the visor pivots about a fixed rear section. In an alternative embodiment, side sections pivot on either side of a fixed central section. Hinges provide the pivoting means for the movable section or sections. The hinges alternate with a number of pairs of fingers and catches, which provide the means for holding a pivotable section in place relative to the fixed section. The aforementioned parts making up the visor are fabricated from a single piece of molded plastic, created by injection molding or other methods practiced in the industry. The device is relatively simple and inexpensive to make and has no parts that are intended to be detached.

The above objects, as well as additional objects, features, and advantages of the invention will become apparent in the following detailed description and in the drawings.

BRIEF DESCRIPTION OF THE DRAWINGS

FIG. 1 is a perspective view of a cap according to the invention, shown with the visor fore section coplanar with the visor rear section.

FIG. 2 is another perspective view of the cap, showing the visor fore section pivoted vertically upwards relative to the visor rear section.

FIG. 3 is yet another perspective view of the cap, showing the visor fore section pivoted vertically downwards relative to the visor rear section.

FIG. 4 is a perspective view of an alternative embodiment of a cap according to the invention.

FIG. 5 is a another perspective view of the cap, showing the halves of the visor fore section pivoted vertically relative to the visor rear section, with each half directed in the opposite direction from the other half.

FIG. 6 is another perspective view of the cap, showing both halves of the visor fore section pivoted vertically upwards relative to the visor rear section.

FIG. 7 is another perspective view of the cap, showing both halves of the visor fore section pivoted vertically upwards relative to the visor rear section.

FIG. 8. is a top plan view of the invention, showing only the internal elements of the visor.

FIG. 9 is a right cross-sectional view thereof, taken along lines 9—9 in FIG. 8.

FIG. 10 is a right cross-sectional view thereof, taken along lines 10—10 in FIG. 8.

FIG. 11 is another right cross-sectional view thereof, showing the visor fore section pivoted and held in an upwardly vertical orientation.

DESCRIPTION OF THE PREFERRED EMBODIMENT

Figure 12:
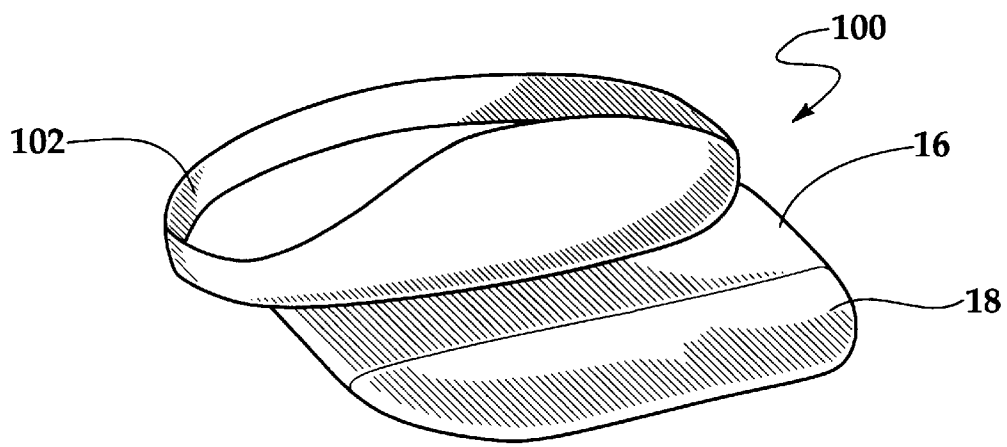
FIG. 12 is a perspective view of another embodiment, for use without a cap, such as a tennis visor.

As shown in FIGS. 1–3, the preferred embodiment 10 for the headgear is a cap having a crown 12 and a visor 14. The visor 14 in turn has a rear section 16 that is fixedly attached to the crown 12 along a first edge 13 and a fore section 18 that is able to pivot about the rear section 16. FIG. 1. shows the fore section 18 positioned in the same plane as the rear section 16, so that the visor 14 has the same appearance as a conventional visor. In FIG. 2, the fore section 18 is shown turned straight up from the rear section 16, while in FIG. 3, the fore section 18 is turned downward. In either position, the fore section 18 can display a printed message or logo (not shown).

FIGS. 4–7 illustrate another embodiment of the invention. In this embodiment, the visor fore section 18 is split into a right half 20 and a left half 22. Each of the halves 20 and 22 is capable of pivoting independently of the other. The figures illustrate some of the possible arrangements for the two halves 20 and 22.

FIGS. 8–11 shows the construction of the visor 14 with the cloth covering 24 of FIGS. 1–7 removed. The visor 14 is preferably made from a single molded piece of a plastic known in the art, such as polyethylene and polypropylene, or a mixture of more than one plastic. A number of functionally identical hinges 26 in the form of a narrow solid strip 28 connects the rear section 16 and fore section 18 together. The hinge 26 uses the plastic's flexibility to achieve the pivot action required. Jointed configurations can also be used, as well as other configurations known in the art that provide a pivotable connection.

Means for engaging and holding the fore section 18 at a specific angle are provided by a number of identical opposed pairs of catches 30 and fingers 32 located along a second edge 34 between the two sections 16 and 18 of the visor 14. The pairs are arranged in an alternating sequence with the hinges 26, and are separated from them by narrow channels 36 and 38. The channels 38 separating the fingers 32 from the visor fore section 18 are not necessary, but they are preferred because they increase the cycle life of the fingers 32, most likely by improving their ability to flex elastically against the catches 30.

Turning in particular to FIGS. 10 and 11, each of the catches 30 has a main beam 40, and two prongs 42 and 44 forming a transverse beam 46 at the end of the main beam 40. The face 48 of the transverse beam 46 distal to the main beam 40 is preferably rounded to allow the corresponding finger 32 to slide easily around the face 48 as the fore section 18 is pivoted. The other face 50 is flat, so that movement of the finger 32 past this face meets greater resistance than for the distal face 48. While only two prongs 42 and 44 are shown, more prongs can be used to permit holding the visor fore section 18 at a greater number of angles than the two transverse angles shown. Other configurations providing a similar ratchet-and-pawl action can also be used.

Each of the fingers 32 has a base 52 that is the same thickness as the visor fore section 18. The base 52 narrows down to a tip 54 that engages the catch 30. While a stepped (non-tapered) narrowing is illustrated, other configurations can also be employed. It is also possible to locate the fingers 32 on the visor rear section 16, with the catches 30 on the visor fore section 18.

Another embodiment 100 for the headgear is illustrated in FIG. 12. This embodiment differs from the preferred embodiment mainly by employing an adjustable headband 102 for holding the headgear on the user's head, rather than a cap with a crown. The second embodiment is identical in all other respects to the preferred embodiment. The second embodiment is envisioned for use in sports such as tennis, where the use of visors without caps is traditional and more widely accepted than in sports such as baseball, where caps are the norm.

Figure 13:
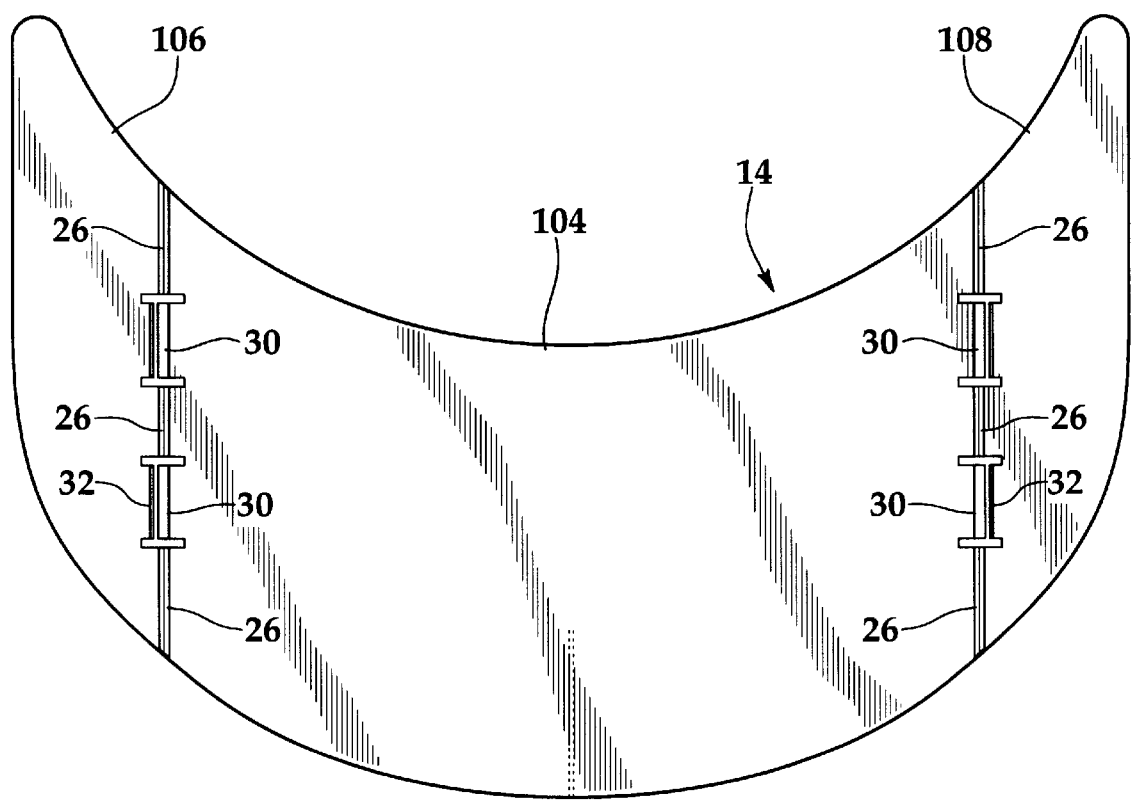
FIG. 13 is a top plan view of another embodiment of the invention, showing only the internal elements of the visor.

FIG. 13 shows an alternative embodiment for the visor 14. In this embodiment, the hinges 26, catches 30, and fingers 32 are arranged on axes running from the front to the back of the visor 14, at right angles to the orientation for these elements in FIGS. 8–11. Thus, in this embodiment there is a fixed center section 104 and two functionally identical pivotable side sections 106 and 108. Other orientations can also be used, as well as a combination of these orientations.

The invention has been shown in several embodiments. It should be apparent to those skilled in the art that the invention is not limited to these embodiments, but is capable of being varied and modified without departing from the scope of the invention as set out in the attached claims.

What is claimed is:

1. A piece of headgear, comprising:
   means for removably attaching the headgear to a user's head;
   a visor having a fixed section and a pivotable section, the fixed section having a first edge and a second edge, the first edge being adapted to attach to the means for removably attaching the headgear to a user's head;
   connecting means interconnecting the fixed section and the pivotable section along the second edge, thereby allowing the pivotable section to be pivoted to a predetermined angle relative to the fixed section;
   wherein the visor and the connecting means are integrally formed from a single piece of plastic material; and
   means for engaging and holding the pivotable section in place at the predetermined angle.

2. A piece of headgear as recited in claim 1, wherein the connecting means is a hinge, and the means for engaging and holding the pivotable section further comprises a finger attached to one of the two visor sections, and a catch attached to the other visor section, the catch being adapted to engage the finger and to resist movement of the finger past the catch.

3. A piece of headgear as recited in claim 2, wherein the catch has a plurality of prongs, each prong being adapted to engage the finger and to hold the finger at a different predetermined angle.

4. A piece of headgear as recited in claim 2, wherein the finger is attached to the pivotable section and the catch is attached to the fixed section.

5. A piece of headgear as recited in claim 1, wherein the means for engaging and holding the pivotable section further comprises a plurality of latches, each latch further comprising a finger attached to one of the two visor sections, and a catch, attached to the other visor section and adapted to engage the finger and to resist movement of the finger past the catch.

6. A piece of headgear as recited in claim 1, wherein the means for removably attaching the headgear to a user's head is a cap having a crown.

7. A piece of headgear as recited in claim 1, wherein the means for removably attaching the headgear to a user's head is an adjustable headband.

8. A piece of headgear as recited in claim 1, wherein the visor, the connecting means and the means for engaging and holding the pivotable section are integrally formed from a single piece of plastic material.

9. A piece of headgear, comprising:
   a crown;
   a visor having two sections: a fixed section attached to the crown along a first edge and a pivotable section pivotably attached to the fixed section with a hinge along a second edge; and
   means for engaging and holding the pivotable section in place at a predetermined angle relative to the fixed section;
   and wherein the visor and the hinge are integrally formed from a single piece of plastic material.

10. A piece of headgear as recited in claim 9, wherein the means for engaging and holding the pivotable section further comprises a finger, attached to the pivotable section, and a catch, attached to the fixed section and adapted to engage the finger and to resist movement of the finger past the catch.

11. A piece of headgear as recited in claim 9, wherein the fixed section, the pivotable section, the hinge, and the means for engaging and holding the pivotable section are integrally formed from a single piece of plastic material.

12. A piece of headgear, comprising:
   means for removably attaching the headgear to a user's head;
   a visor having a fixed section and a pivotable section, the fixed section having a first edge and a second edge, the first edge being adapted to attach to the means for removably attaching the headgear to a user's head;
   connecting means interconnecting the fixed section and the pivotable section along the second edge, thereby allowing the pivotable section to be pivoted to a predetermined angle relative to the fixed section; and means for engaging and holding the pivotable section in place at the predetermined angle;

wherein the visor and the means for engaging and holding the pivotable section are integrally formed from a single piece of plastic material.

13. A piece of headgear as recited in claim 12, wherein the connecting means is a hinge, and the latching means further comprises a finger attached to one of the two visor sections, and a catch attached to the other visor section, the catch being adapted to engage the finger and to resist movement of the finger past the catch.

14. A piece of headgear as recited in claim 13, wherein the catch has a plurality of prongs, each prong being adapted to engage the finger and to hold the finger at a different predetermined angle.

15. A piece of headgear as recited in claim 13, wherein the finger is attached to the pivotable section and the catch is attached to the fixed section.

16. A piece of headgear as recited in claim 12, wherein the latching means further comprises a plurality of latches, each latch further comprising a finger attached to one of the two visor sections, and a catch, attached to the other visor section and adapted to engage the finger and to resist movement of the finger past the catch.

17. A piece of headgear as recited in claim 12, wherein the means for removably attaching the headgear to a user's head is a cap having a crown.

18. A piece of headgear as recited in claim 12, wherein the means for removably attaching the headgear to a user's head is an adjustable headband.

19. A piece of headgear as recited in claim 12, wherein the visor, the connecting means and the means for engaging and holding the pivotable section are integrally formed from a single piece of plastic material.

* * * * *